United States Patent [19]

Vaillant et al.

[11] Patent Number: 4,518,404
[45] Date of Patent: May 21, 1985

[54] APPARATUS FOR GENERATING AN AEROSOL

[76] Inventors: Michael Vaillant, Kleppingstr. 9-11, D-4600 Dortmund; Günter Klarhorst, Eisgrundstr. 7, D-4800 Bielefeld, both of Fed. Rep. of Germany

[21] Appl. No.: 519,526

[22] Filed: Aug. 1, 1983

[30] Foreign Application Priority Data

Aug. 6, 1982 [DE] Fed. Rep. of Germany ... 8222263[U]
Jun. 3, 1983 [DE] Fed. Rep. of Germany ... 8316307[U]

[51] Int. Cl.³ ............................................. B01D 46/00
[52] U.S. Cl. ....................................... 55/256; 55/279; 128/200.16; 261/DIG. 65
[58] Field of Search ................. 55/220, 279, 256, 259; 128/200.16; 239/102, 338; 261/1, 81, DIG. 48, DIG. 65; 218/169

[56] References Cited

U.S. PATENT DOCUMENTS 3,970,250 7/1976 Drews .................................. 239/102
4,159,803 7/1979 Cameto et al. ...................... 239/102
4,285,813 8/1981 Stewodt et al. ..................... 210/169
4,377,399 3/1983 Bryson .................... 261/DIG. 65 X

FOREIGN PATENT DOCUMENTS 2843756 4/1980 Fed. Rep. of Germany .
1035049 7/1966 United Kingdom ........... 128/200.16

Primary Examiner—Charles Hart
Attorney, Agent, or Firm—Collard, Roe & Galgano

[57] ABSTRACT

An apparatus for generating an aerosol is provided which includes an atomizing chamber, an aerating wheel and an annular bacteria filter each of which must be sterilized in an autoclave or sterilizer, connected into a modular unit and releasably disposed of through a plug connection on the outer side of the housing. The air supply openings formed in the wall of the aerating wheel chamber, which serve to establish communication between the annular filter chamber and the aerating wheel chamber, may be reduced in a stepless manner by a slidable closure ring. By this regulation of the air supply, the mechanism can also be used for respiration.

20 Claims, 4 Drawing Figures

APPARATUS FOR GENERATING AN AEROSOL

The present invention relates to an apparatus for generating an aerosol, including an atomizing chamber scattering a liquid by means of an oscillation generator and discharging the aerosol, an aerating wheel driven by a motor located in a separate chamber which draws in air through a bacteria filter and supplies the drawn in air through a separate connection circuit to the upper portion of the atomizing chamber. The aerating wheel is connected to the motor by a magnetic coupling effective through a separating wall disposed between the motor and the aerating wheel.

An aerosol is a gas, particularly air, which contains solid or fluid suspended particles in the most finely distributed form. Aerosols from water and water solutions having droplets of a size of 1 to 5 $\mu$m are frequently used in medicine, and wherein water soluble medications can be added to the watery solutions for manufacturing the aerosol. The aerosols consisting of water and watery solutions used in medicine serve, amongst other purposes, for increasing the air moisture in surgery rooms and intensive care locations, and to moisten the breathing tract of patients. Here it is essential that the aerosols be free of bacteria, so as to avoid possible infections. Aerosols free of bacteria can, however, only be obtained with devices which are free of bacteria themselves.

A mechanism of the aforedescribed kind is shown and described in DE-AS No. 2843756. In this mechanism, the aerating wheel is disposed in a replaceable holder which is displaceably arranged in a guide frame of the housing, and may be arrested. With the aid of spring leaves and recesses this holder may be set into its operating position. A bacteria filter is precoupled to the entry opening of the aerating wheel chamber. The bacteria filter must be tightly coupled to the entry opening so as to avoid suctioning in of air which bypasses the bacteria filter.

The bacteria filter disposed in the suction opening for the aerating wheel cannot prevent the accumulation in the aerating wheel, and in the space surrounding it, of any illness inciters which pass through the atomizing chamber into the aerosol and which represent a danger of infection. This risk occurs primarily if the bacteria filter is not tightly coupled. A frequent autoclaving of the aerating holder and of the bacteria filter is required. For this purpose, the bacteria filter must first be laterally removed from the housing, and subsequently the holder must be slid out from the housing in an upward direction.

So that the entire arrangement always remains fully functional, three separate parts, namely the atomizing chamber, the aerating wheel holder and the bacteria filter must each be removed and sterilized in an autoclave or sterilizer. This is time-consuming and requires extreme care. There is no guarantee that all the separate parts are always made completely sterile, and inserted so as to be fully functional. It is primarily left to the care of the appropriate personnel that all parts are sterile and properly reinserted. Regulation of the air supply is not possible in such prior art mechanisms.

It is, therefore, an object of the present invention to produce a device of the aforedescribed kind, so that the manipulation with respect to the removal and insertion of the elements for the purpose of passing them to the autoclave or sterilizer are reduced to a minimum. Also, that it is ensured that the atomizing chamber, the aerating wheel, and the bacteria filter are sterilized to the same degree, and are always fully functional after insertion, and that the air supply may be regulated in a stepless manner.

The above objects are accomplished, according to the present invention, by the atomizing chamber, the aerating wheel and the bacteria filter being united in a modular unit, by their being releasably disposed on the outer side of the housing, and wherein the air supply openings to the aerating wheel chamber are closeable by a displaceable closure ring.

By the arrangement according to the present invention, only one element must be made sterile. It is impossible to forget one of the elements during the passage to the autoclave or to the sterilizer. Substantial advantages are obtained by the shortened insertion and removal time, while ensuring a trouble-free operation. Due to the possibility of reducing the air supply openings to zero in a stepless manner by means of a displaceable closure ring, the velocity of the fog guidance can be regulated. Furthermore, the mechanism can be used as a respirator when the air supply is dispensed with. For this purpose, a connection to a container with enriched oxygen is obtained through a Y connection element, wherein the fog arising in the atomizing chamber is taken along by the oxygen and, therefore, an increase in the moisture of the oxygen is obtained. By an inclined arrangement of the quartz disc, a substantial increase in the generation of the aerosol is possible with a minimum of effort at the same energy consumption.

The present invention will be described and understood more readily when considered together with the accompanying drawings, in which.

Figure 1:
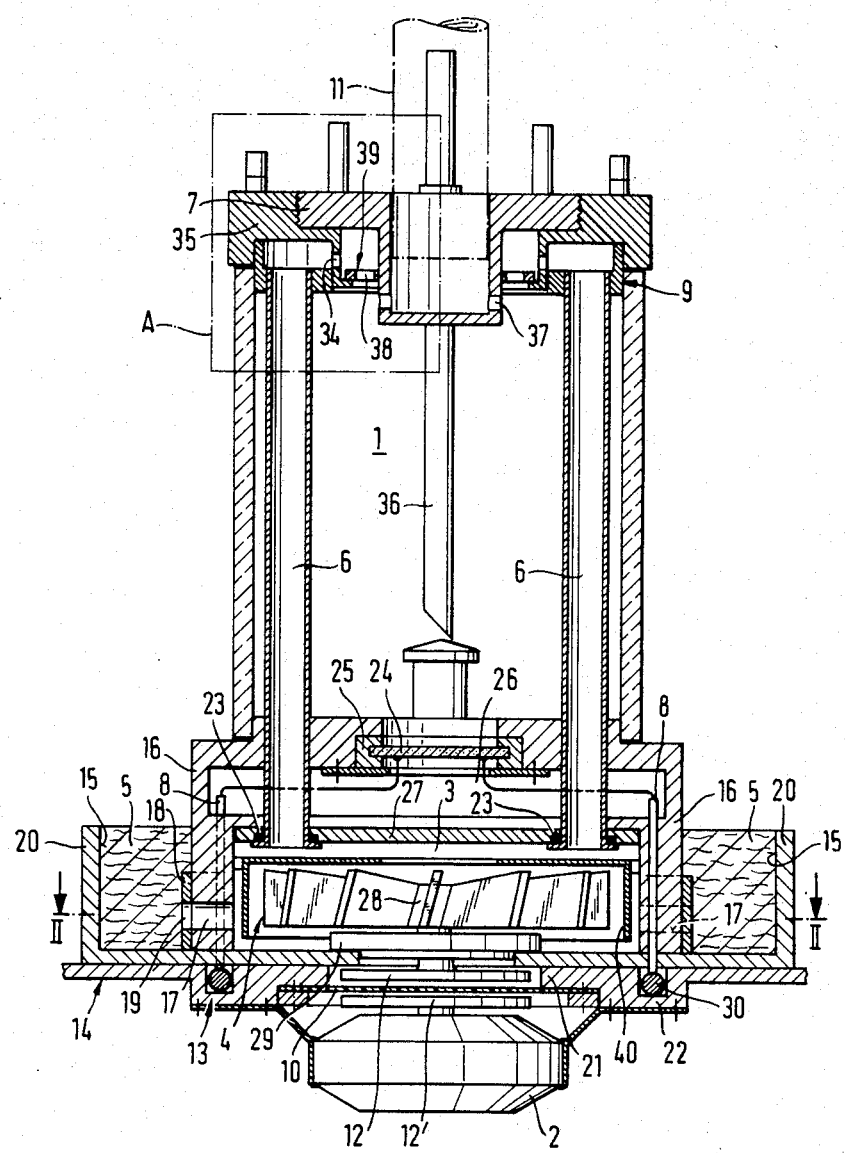
FIG. 1 is a schematic vertical section through the essential parts of the mechanism of the present invention.
Figure 2:
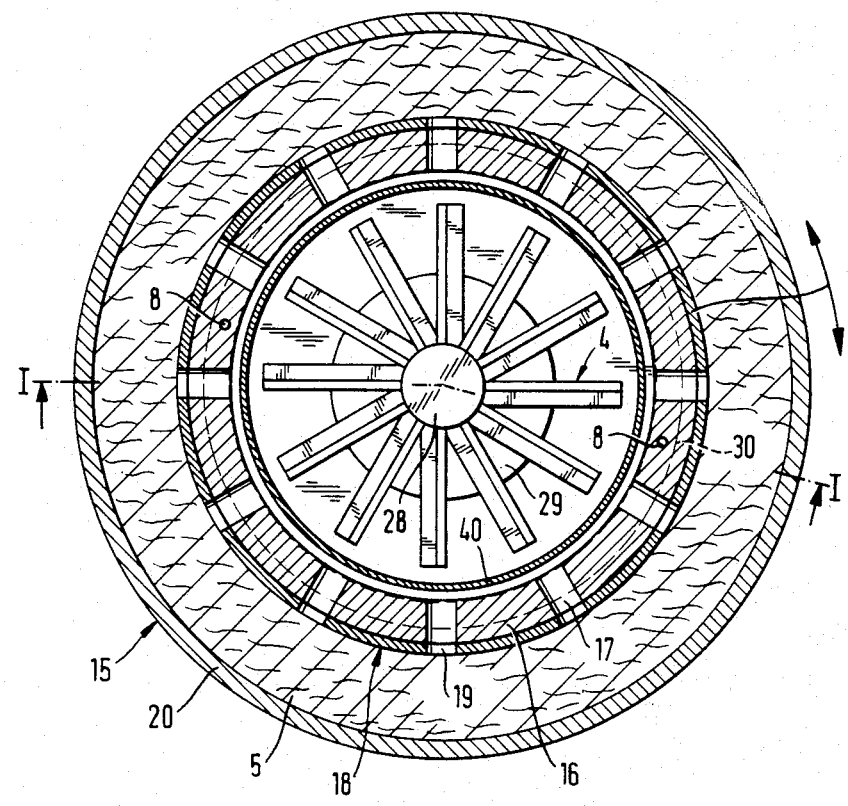
FIG. 2 is a horizontal section along the line A—B of FIG. 1.

As can be seen in FIGS. 1 and 2, in housing 14 of the mechanism there is provided an aerating wheel chamber 3 for receiving an aerating wheel 4. Wall 16 of aerating wheel chamber 3 is extended beyond the aerating wheel chamber upwardly and serves as a lateral limitation for oscillation chamber 26, as well as a receiver for atomizing chamber 1 which is formed of a glass cylinder set thereon. Exterior to wall 16 of aerating wheel chamber 3 there is disposed a filter chamber 15 surrounding it, in which a bacteria filter 5 formed as a ring filter is replaceably supported. Atomizing chamber 1 with aerating wheel 4, and filter chamber 15 with bacteria filter 5 disposed therein, form a modular unit, which is connected to housing 14 by means of a plug connection 13.

In wall 16 of aerating wheel chamber 3 there are provided air openings 17 distributed around the periphery at uniform distances. A displaceable closure ring 18 extending around air supply openings 17 serves to regulate the air supply. Openings 19 are provided in closure ring 18 and are aligned with air supply openings 17 in wall 16 of aerating wheel chamber 3. It is advantageous if the filter chamber 15 is open upwardly, and wherein the filter chamber wall 20 ends approximately at the height of floor 27 of oscillation chamber 26.

Scattering of the liquid is accomplished in atomizing chamber 1 with the aid of an ultrasonic scattering effect, wherein the liquid is excited to longitudinal oscillations. A quartz disc 24 with a holder ring 25 serves as a generator of ultrasonic oscillations. The quartz ring 24 is disposed at the lower border of atomizing chamber 1 in oscillation chamber 26 whose floor 27 forms the upper closure of aerating wheel chamber 3. The liquid to be scattered may be water or a watery solution with water soluble medications. A delivery hose 11 is connected to atomizing chamber 1 from which the aerosol is discharged and which may optionally be supplied to the breathing organ of a patient. The aerosol can also be supplied to the surrounding air with or without discharge hose 11. The use of the inventive arrangement is not limited to the medical community. It can also be used where increase of air moisture is desirable or required, for example, in the food industry, in processing of leather, in museums, libraries, and EDV rooms. Furthermore, within certain limits, optical effects can also be obtained.

Motor 2, which can be driven by any arbitrary energy source, for example, by a battery, is separated from aerating wheel chamber 3 in an air-tight and water-tight manner by a security foil 10. Security foil 10 is rigidly disposed below a peripheral reinforcement 21 of housing 14. This air-tight and water-tight separation can also be accomplished by means of the continuous housing 14, which is reduced in thickness at an appropriate location.

The connection between motor 2 and aerating wheel 4 is accomplished by a magnetic coupling. This magnetic coupling consists of two magnetic discs, 12 and 12'. Aerating wheel 4 is an axial aerator, which draws in air radially and discharges it axially. The bearing of aerating wheel 4 is designated with the reference numeral 28, and the bearing support with the reference numeral 29.

In atomizing chamber 1, there are disposed two vertically extending air channels 6 for supplying air into the upper part of atomizing chamber 1. Air channels 6 are connected in an air-tight and water-tight manner to the floor of oscillation chamber 26 by respective sealing rings 23. The air channels are connected to a holder ring 9 at the upper end, on which there is disposed a distributor- and receiving-ring 35 provided with openings 34 for the cover 7 of atomizing chamber 1, which serves as the receiver for discharge hose 11. A level-indicating tube 36 is disposed on the distributor- and receiving-ring 35. Outlet openings 37 are provided on the cover 7 of the chamber. Outlet openings 37 of chamber cover 7 are disposed at a distance from the upper border, and wherein a ring collar disc 39 provided with openings 38 is provided above the outlet openings 37. The cover for housing 14 is hingedly connected thereto.

Plug connection 13 is formed by vertically extending electrical contact conduits 8, which are connected to a contact ring 30, which in turn is supported in an annular bulge 22 of housing 14. In order to avoid any air cross currents, a sealing disc may be disposed between filter chamber 15 and the upper side of the cover of housing 14. As clearly seen in FIG. 1, a forceable guidance 40 for the air drawn in and passing from air supply openings 17 to the upper side of aerating wheel 4 is visible.

Figure 3:
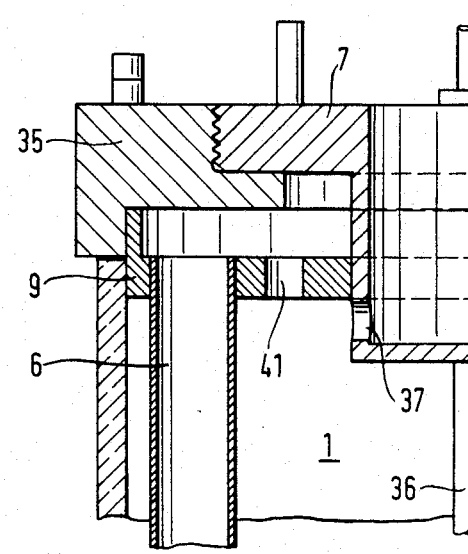
FIG. 3 is an enlarged representation of the area designated A of FIG. 1, showing an alternate embodiment.

As seen in the alternate embodiment of FIG. 3, there are provided in holder ring 9 apertures 41 for supplying air to atomizing chamber 1. In this embodiment, in the distributor- and receiving-ring 35, openings 34 as well as the arrangement of the ring collar disc 39 can be dispensed with. By the arrangement of apertures 41 in the holder ring 9, a substantially more uniform distribution of air and therefore an improved aerosol is achieved, while avoiding formation of condensation at the inner wall of atomizing chamber 1.

Figure 4:
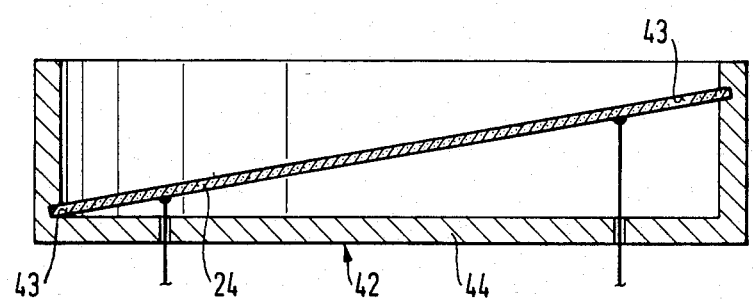
FIG. 4 is an enlarged vertical section through a quartz disc inclined in a holder ring.

According to FIG. 4, the quartz disc 24 is shown inclined to the horizontal. For this purpose, it is supported in a holder ring 42, which is formed on an inner side thereof with a recess preferably inclined by 10 degrees for inserting the quartz disc 24. For an improved support, the holder ring 42 is provided with a continuous flow plate 44.

It is to be understood that the foregoing general and detailed descriptions are explanatory of the present invention and are not to be interpreted as restrictive of the scope of the following claims.

What is claimed is:

1. An apparatus for generating an aerosol, comprising:
    (a) a housing for said apparatus;
    (b) a motor mounted in said housing;
    (c) an atomizing chamber for discharging and scattering the aerosol by means of an oscillation generator;
    (d) an aerating wheel chamber separated from said atomizing chamber;
    (e) an aerating wheel disposed in said aerating wheel chamber which passes drawn in air to the upper part of said atomizing chamber by means of conduits;
    (f) a filter chamber disposed about the periphery of said aerating wheel chamber;
    (g) a bacteria filter for filtering the air drawn in by said aerating wheel replaceably housed in said filter chamber; said atomizing chamber, said aerating wheel chamber and aerating wheel, and said filter chamber and bacteria filter being united in a modular unit releasably connected on the outer side of said housing;
    (h) an air-tight and water-tight separating wall of said housing disposed between said motor and said aerating wheel;
    (i) a magnetic coupling acting through said separating wall connecting said motor to said aerating wheel to drive said aerating wheel; and
    (j) means for regulating the supply of drawn in air to said aerating wheel.

2. The apparatus according to claim 1, wherein said atomizing chamber is disposed vertically on said chamber containing said aerating wheel.

3. The apparatus according to claim 1, wherein said aerating wheel is an axial aerator.

4. The apparatus according to claim 1, wherein said motor is driven by a battery.

5. The apparatus according to claim 1, wherein said air-tight and water-tight separating wall between the motor and the aerating wheel chamber is formed by a security foil.

6. The apparatus according to claim 5, wherein said security foil is rigidly disposed below a peripherally-extending reinforcement of the housing.

7. The apparatus according to claim 1, wherein said oscillation generator is disposed below said atomizing chamber in a separate oscillation chamber whose floor forms the upper closure of said aerating wheel chamber.

8. The apparatus according to claim 7, wherein said conduit means for passing drawn in air from said aerating wheel chamber to the upper part of said atomizing chamber includes at least one vertically extending air channel.

9. The apparatus according to claim 8, wherein said air channels disposed in said atomizing chamber are connected to the floor of said oscillating chamber in an air-tight and water-tight manner by means of respective sealing rings.

10. The apparatus according to claim 9, which further includes a sealing disc disposed between said filter chamber and the upper edge of said housing.

11. The apparatus according to claim 9, which further includes a forceable guidance for the air drawn in, disposed from the air supply openings to the upper side of the aerating wheel.

12. The apparatus according to claim 9, which further includes a ring holder at the upper part of said atomizing chamber for holding said vertically extending air channels and having apertures formed therein for supplying air to the atomizing chamber.

13. The apparatus according to claim 1, wherein said oscillation generator includes a quartz disc disposed in said oscillation chamber being inclined to the horizontal.

14. The apparatus according to claim 13, wherein said quartz disc is inclined to the horizontal at an angle of 10 degrees.

15. The apparatus according to claim 13, wherein an inclined inner recess is formed in the inner periphery of a holding ring for receiving said quartz disc.

16. The apparatus according to claim 1, wherein said modular unit is connected to the outer side of said housing by means of a plug connection.

17. The apparatus according to claim 16, wherein said plug connection is formed by vertically extending electrical contact conduits which are connected to a contact ring supported in an annular bulge in said housing.

18. The apparatus according to claim 1, wherein the wall of said aerating wheel chamber separating said chamber from said filter chamber is formed with air supply openings communicating between said chambers, and the means for regulating the supply of drawn in air to said aerating wheel comprises a displaceable closure ring disposed around said air supply openings having openings therein corresponding to said air supply openings.

19. The apparatus according to claim 18, wherein said air supply openings are disposed at uniform distances from one another.

20. The apparatus according to claim 18, wherein said openings in said closure ring are aligned with the air supply openings in the aerating wheel chamber.

* * * * *